(12) United States Patent
Munte et al.

(10) Patent No.: US 12,422,841 B2
(45) Date of Patent: Sep. 23, 2025

(54) METHODS AND SYSTEMS FOR PRECONDITIONING A VEHICLE PRIOR TO A VEHICLE-SHARING SESSION

(71) Applicants: DENSO International America, Inc., Southfield, MI (US); DENSO CORPORATION, Aichi (JP)

(72) Inventors: Christian Munte, Southfield, MI (US); Martin Nespolo, Gross Pointe Woods, MI (US); Nandhinee Kandasamy, Novi, MI (US); Mustafa Mahmoud, Farmington, MI (US)

(73) Assignees: DENSO International America, Inc., Southfield, MI (US); DENSO CORPORATION, Kariya (JP)

( * ) Notice: Subject to any disclaimer, the term of this patent is extended or adjusted under 35 U.S.C. 154(b) by 679 days.

(21) Appl. No.: 17/218,409

(22) Filed: Mar. 31, 2021

(65) Prior Publication Data

US 2022/0026898 A1    Jan. 27, 2022

Related U.S. Application Data

(60) Provisional application No. 63/055,527, filed on Jul. 23, 2020.

(51) Int. Cl.
 *G05D 1/00* (2024.01)
 *B60H 1/00* (2006.01)
  (Continued)

(52) U.S. Cl.
 CPC ....... *G05D 1/0011* (2013.01); *B60H 1/00657* (2013.01); *B60H 1/00892* (2013.01);
  (Continued)

(58) Field of Classification Search
 CPC .............. G05D 1/0011; B60H 1/00657; B60H 1/00892; B60H 1/00735; B60H 1/00778;
  (Continued)

(56) References Cited

U.S. PATENT DOCUMENTS 9,428,034 B2 *  8/2016  Yang ................... B60H 1/00742
10,299,520 B1 *  5/2019  Shaffer ................ A61B 5/6804
 (Continued)

FOREIGN PATENT DOCUMENTS

EP           3163068        9/2018

*Primary Examiner* — Vivek D Koppikar
*Assistant Examiner* — Dominick Mulder
(74) *Attorney, Agent, or Firm* — Harness, Dickey & Pierce, P.L.C.

(57) ABSTRACT

A method of remotely activating a vehicle system of a vehicle, the vehicle being part of a vehicle-share enterprise, the method including generating a control signal based on session parameters associated with a vehicle-sharing session, preconditioning parameters associated with the vehicle-sharing session, and sensor data associated with the vehicle-sharing session, where the sensor data includes vehicle sensor data from one or more sensors of the vehicle associated with the vehicle-sharing session, client device sensor data from one or more sensors of a client device, or a combination thereof. The method includes, prior to initiating the vehicle-sharing session, broadcasting the control signal to the vehicle, where the control signal is configured to selectively control the vehicle system.

25 Claims, 5 Drawing Sheets

(51) Int. Cl.
  *B60R 16/023* (2006.01)
  *B60R 16/037* (2006.01)
  *G05B 13/04* (2006.01)
  *G06Q 30/0283* (2023.01)
  *G06Q 50/40* (2024.01)
  *A61B 5/00* (2006.01)

(52) U.S. Cl.
  CPC .......... *B60R 16/023* (2013.01); *B60R 16/037* (2013.01); *G05B 13/048* (2013.01); *G06Q 30/0283* (2013.01); *G06Q 50/40* (2024.01); *A61B 5/6893* (2013.01); *G06Q 2240/00* (2013.01)

(58) Field of Classification Search
  CPC ... B60R 16/023; B60R 16/037; B60R 25/209; G05B 13/048; G06Q 30/0283; G06Q 50/30; G06Q 2240/00; A61B 5/6893; B60K 2370/48; B60K 2370/55
  USPC .......................................................... 701/2
  See application file for complete search history.

(56) References Cited

U.S. PATENT DOCUMENTS

| | | | |
|---|---|---|---|
| 10,554,759 B2 | 2/2020 | Penilla et al. | |
| 11,481,819 B2* | 10/2022 | Igata | G06Q 30/0283 |
| 2008/0117079 A1* | 5/2008 | Hassan | F02N 11/101 |
| | | | 340/901 |
| 2014/0222253 A1* | 8/2014 | Siegel | B60R 16/037 |
| | | | 701/2 |
| 2017/0028949 A1* | 2/2017 | Nelson | G01C 21/362 |
| 2017/0061508 A1* | 3/2017 | Sen | G06Q 20/20 |
| 2017/0139384 A1* | 5/2017 | Takeuchi | G06Q 30/0631 |
| 2017/0190318 A1* | 7/2017 | Imamura | H04W 76/11 |
| 2017/0210201 A1* | 7/2017 | Green | B62D 15/025 |
| 2017/0253201 A1* | 9/2017 | Maeshiro | B60R 16/037 |
| 2018/0045474 A1* | 2/2018 | Yoshikawa | F24F 11/56 |
| 2018/0136656 A1* | 5/2018 | Rasmusson, Jr. | |
| | | | B60W 60/00253 |
| 2018/0137593 A1* | 5/2018 | Djuric | G06Q 50/40 |
| 2018/0178797 A1* | 6/2018 | Seaman | G06Q 10/083 |
| 2018/0218470 A1* | 8/2018 | Belwafa | G06Q 10/02 |
| 2018/0266834 A1* | 9/2018 | Cronin | B60W 50/14 |
| 2018/0342035 A1* | 11/2018 | Sweeney | G06Q 50/40 |
| 2019/0089194 A1* | 3/2019 | Okita | H02J 3/14 |
| 2019/0164421 A1* | 5/2019 | Lauer | G08G 1/096775 |
| 2019/0168584 A1* | 6/2019 | Seiferlein | B60H 1/00828 |
| 2019/0215370 A1* | 7/2019 | Granda | H04L 67/12 |
| 2019/0390867 A1* | 12/2019 | Lee | F24F 11/64 |
| 2020/0062076 A1* | 2/2020 | Elson | B60H 1/00735 |
| 2020/0150646 A1* | 5/2020 | Sugimoto | G06Q 20/145 |
| 2020/0269809 A1* | 8/2020 | Sanji | B60R 25/31 |
| 2020/0283000 A1* | 9/2020 | Schön | B60W 40/08 |
| 2020/0393573 A1* | 12/2020 | Solin | G01C 21/206 |
| 2021/0001806 A1* | 1/2021 | Kim | B60R 25/24 |
| 2021/0061202 A1* | 3/2021 | Ye | B60R 16/037 |
| 2021/0140670 A1* | 5/2021 | Matsuura | F24F 11/63 |
| 2021/0164676 A1* | 6/2021 | Huang | F24F 11/56 |

* cited by examiner

METHODS AND SYSTEMS FOR PRECONDITIONING A VEHICLE PRIOR TO A VEHICLE-SHARING SESSION

CROSS-REFERENCE TO RELATED APPLICATIONS

This application claims the benefit of and priority to U.S. Provisional Application No. 63/055,527 filed on Jul. 23, 2020. The disclosure of the above application is incorporated herein by reference.

FIELD

The present disclosure relates to systems and methods for preconditioning a vehicle prior to a vehicle-sharing session.

BACKGROUND

The statements in this section merely provide background information related to the present disclosure and may not constitute prior art.

Vehicle-sharing fleet managers may have a variety of vehicles that are available to rent for a predefined period of time using a vehicle-sharing application. Furthermore, prior to initiating the vehicle-sharing session, a user may desire to precondition the vehicle, which may include controlling an interior setpoint temperature of the vehicle, a defrost setting of the vehicle, a seat position of the vehicle, an audio setting of the vehicle, among other adjustable and/or customizable features of the vehicle. However, it may be undesirable to precondition the vehicle in certain scenarios. As an example, it may be undesirable to control the interior setpoint temperature of the vehicle in advance of the vehicle-sharing session when the vehicle is located in an enclosed structure, such as a parking garage.

SUMMARY

This section provides a general summary of the disclosure and is not a comprehensive disclosure of its full scope or all of its features.

The present disclosure provides a method of remotely activating a vehicle system of a vehicle, the vehicle being part of a vehicle-share enterprise, the method including generating a control signal based on session parameters associated with a vehicle-sharing session, preconditioning parameters associated with the vehicle-sharing session, and sensor data associated with the vehicle-sharing session, where the sensor data includes vehicle sensor data from one or more sensors of the vehicle associated with the vehicle-sharing session, client device sensor data from one or more sensors of a client device, or a combination thereof. The method includes, prior to initiating the vehicle-sharing session, broadcasting the control signal to the vehicle, where the control signal is configured to selectively control the vehicle system.

In some forms, the session parameters include a start time of the vehicle-sharing session, an end time of the vehicle-sharing session, a monetary cost of the vehicle-sharing session, a location associated with a vehicle-sharing session request, or a combination thereof.

In some forms, the preconditioning parameters include a setpoint temperature of the vehicle, a defrost setting of the vehicle, a seat position of the vehicle, an audio setting of the vehicle, or a combination thereof.

In some forms, the vehicle sensor data is indicative of an accumulation of snow, an accumulation of ice, or a combination thereof, the one or more sensors of the vehicle include at least one of a light sensor, a sound sensor, or a combination thereof, and the control signal includes instructions for selectively controlling a defrost system, as the vehicle system, based on the vehicle sensor data.

In some forms, the vehicle sensor data is indicative of a cabin temperature of the vehicle, the one or more sensors of the vehicle include one or more temperature sensors, and the control signal includes instructions for selectively controlling a climate control system, as the vehicle system, based on the vehicle sensor data.

In some forms, the vehicle sensor data is indicative of a steering wheel temperature of the vehicle, a seat temperature of the vehicle, or a combination thereof, the one or more sensors of the vehicle include one or more temperature sensors, and the control signal includes instructions for selectively controlling a climate control system, as the vehicle system, based on the vehicle sensor data.

In some forms, the vehicle sensor data is indicative of ambient air characteristics of the vehicle, the one or more sensors of the vehicle include an air quality sensor, and the control signal includes instructions for selectively controlling an ignition system, as the vehicle system, based on the vehicle sensor data.

In some forms, the vehicle sensor data is indicative of a location of the vehicle, an orientation of the vehicle, or a combination thereof, the one or more sensors of the vehicle include a location sensor, a light sensor, an orientation sensor, an image sensor, a sound sensor, a suspension sensor, or a combination thereof, and the control signal includes instructions for selectively controlling an ignition system, as the vehicle system, based on the vehicle sensor data.

In some forms, the location of the vehicle indicates whether the vehicle is located in an enclosed environment.

In some forms, the client device sensor data is indicative of a location of the client device, a speed of the client device, a direction of the client device, or a combination thereof, and the one or more sensors of the client device include a location sensor, an accelerometer, or a combination thereof.

In some forms, the client device sensor data is indicative of one or more biometrics associated with a user of the client device, and the one or more sensors of the client device include a biometric sensor.

In some forms, the control signal is further based on a prediction model associated with the vehicle, the client device, or a combination thereof.

The present disclosure provides a method of remotely activating a vehicle system of a vehicle, the vehicle being part of a vehicle-share enterprise, the method including generating a control signal based on session parameters associated with a vehicle-sharing session, preconditioning parameters associated with the vehicle-sharing session, and sensor data associated with the vehicle-sharing session, where the sensor data includes vehicle sensor data from one or more sensors of the vehicle associated with the vehicle-sharing session, client device sensor data from one or more sensors of a client device, or a combination thereof. The method includes, prior to initiating the vehicle-sharing session, broadcasting the control signal to the vehicle, identifying the vehicle system from among a plurality of vehicle systems based on the control signal, and controlling the vehicle system based on the control signal.

In some forms, the session parameters include a start time of the vehicle-sharing session, an end time of the vehicle-sharing session, a monetary cost of the vehicle-sharing session, a location associated with a vehicle-sharing session request, or a combination thereof. In some forms, the preconditioning parameters include a setpoint temperature of the vehicle, a defrost setting of the vehicle, a seat position of the vehicle, an audio setting of the vehicle, or a combination thereof.

In some forms, the vehicle sensor data is indicative of an accumulation of snow, an accumulation of ice, or a combination thereof, the one or more sensors of the vehicle include at least one of a light sensor, a sound sensor, or a combination thereof, and the control signal includes instructions for selectively controlling a defrost system, as the vehicle system, based on the vehicle sensor data.

In some forms, the vehicle sensor data is indicative of a cabin temperature of the vehicle, the one or more sensors of the vehicle include one or more temperature sensors, and the control signal includes instructions for selectively controlling a climate control system, as the vehicle system, based on the vehicle sensor data.

In some forms, the vehicle sensor data is indicative of ambient air characteristics of the vehicle, the one or more sensors of the vehicle include an air quality sensor, and the control signal includes instructions for selectively controlling an ignition system, as the vehicle system, based on the vehicle sensor data.

In some forms, the vehicle sensor data is indicative of a location of the vehicle, an orientation of the vehicle, or a combination thereof, the one or more sensors of the vehicle include a location sensor, a light sensor, an orientation sensor, an image sensor, a sound sensor, a suspension sensor, or a combination thereof, and the control signal includes instructions for selectively controlling an ignition system, as the vehicle system, based on the vehicle sensor data.

In some forms, the client device sensor data is indicative of a location of the client device, a speed of the client device, a direction of the client device, or a combination thereof, and the one or more sensors of the client device include a location sensor, an accelerometer, or a combination thereof.

The present disclosure provides a system of remotely activating a vehicle system of a vehicle, the vehicle being part of a vehicle-share enterprise, where the system includes a processor and a nontransitory computer-readable medium including machine-readable instructions that are executable by the processor. The machine-readable instructions include generating a control signal based on session parameters associated with a vehicle-sharing session, preconditioning parameters associated with the vehicle-sharing session, and sensor data associated with the vehicle-sharing session, where the sensor data includes vehicle sensor data from one or more sensors of the vehicle associated with the vehicle-sharing session, client device sensor data from one or more sensors of a client device, or a combination thereof. The machine-readable instructions include, prior to initiating the vehicle-sharing session, broadcasting the control signal to the vehicle, identifying the vehicle system from among a plurality of vehicle systems based on the control signal, and controlling the vehicle system based on the control signal.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
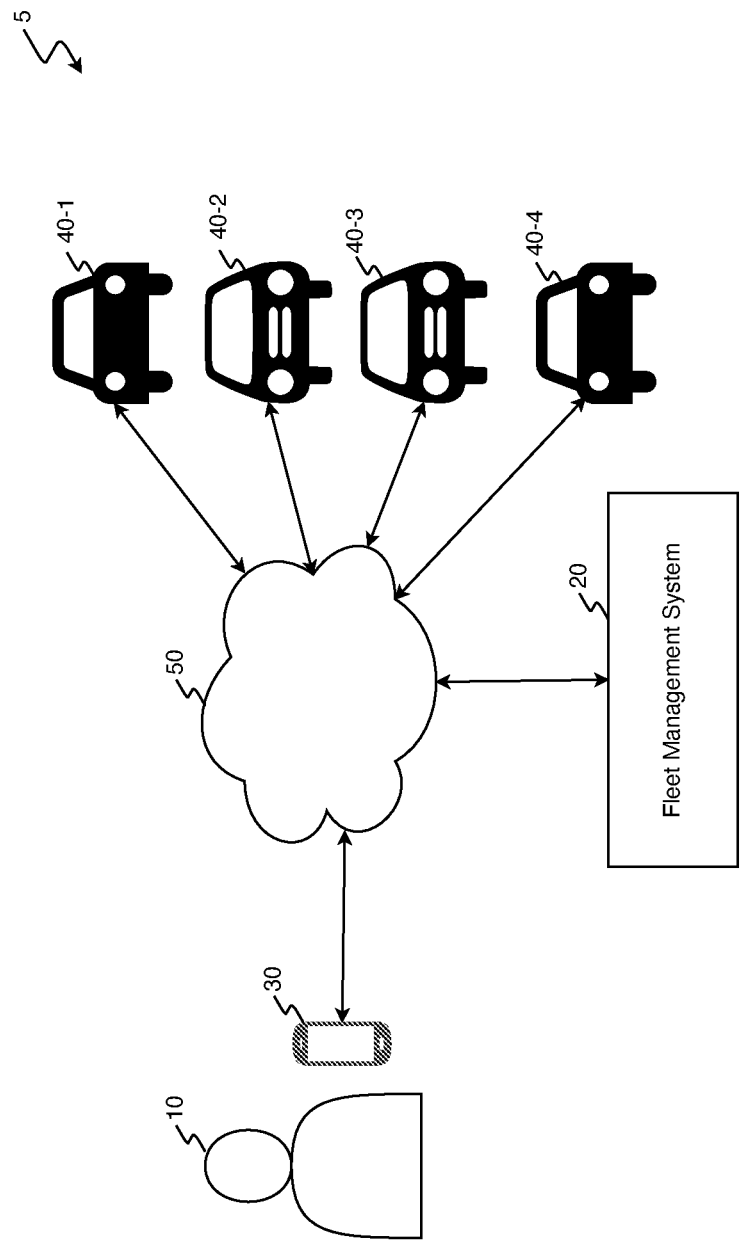
FIG. 1 illustrates a vehicle-sharing system in accordance with the teachings of the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

The present disclosure relates to systems and methods for remotely activating a vehicle system of a vehicle that is part of a vehicle-share enterprise. A fleet management system generates a control signal based on session parameters associated with a vehicle-sharing session, preconditioning parameters associated with the vehicle-sharing session, and sensor data associated with the vehicle-sharing session. The sensor data includes data from a vehicle and/or a client device associated with the vehicle-sharing session. Prior to initiating the vehicle-sharing session, the fleet management system broadcasts the control signal to the vehicle to selectively control the vehicle system. As such, the vehicle-sharing system is configured to remotely precondition the vehicle while accommodating for the location and the environment surrounding the vehicle.

As used herein, "preconditioning" refers to remotely activating a component/system of a vehicle from the vehicle fleet 40 prior to initiating a vehicle-sharing session. As an example, preconditioning the vehicle may include setting an interior setpoint temperature of the vehicle, a defrost setting of the vehicle, a seat position of the vehicle, an audio or infotainment setting of the vehicle, among other adjustable/customizable features of the vehicle. It should be understood that preconditioning the vehicle may include remotely activating any type of vehicle component/system and is not limited to the examples provided herein.

Referring to FIG. 1, a vehicle-sharing system 5 is provided. The vehicle-sharing system 5 generally includes a user 10, a fleet management system 20, a client device 30, and vehicles 40-1, 40-2, 40-3, 40-4 (collectively referred to herein as "vehicle fleet 40"). In one form, the fleet management system 20, the client device 30, and the vehicle fleet 40 are communicably coupled via a network 50 and using one or more wireless communication protocols (e.g., a Bluetooth®-type protocol, a cellular protocol, a wireless fidelity (Wi-Fi)-type protocol, a near-field communication (NFC) protocol, an ultra-wideband (UWB) protocol, among others). While the vehicle fleet 40 illustrates four vehicles, it should be understood that the vehicle fleet 40 may include any number of vehicles in other forms.

In one form, the client device 30 is a computing device that utilizes a wireless communication protocol to generate a vehicle-sharing request. The client device 30 may include, but is not limited to, a computer, laptop, smartphone, tablet, personal digital assistant (PDA), and/or a wearable device. In one form, the user 10 may generate a vehicle-sharing request based on session parameters and/or preconditioning parameters inputted by the user 10 using the client device 30. As an example, the session parameters include a start time of the vehicle-sharing session, an end time of the vehicle-sharing session, a monetary cost of the vehicle-sharing session, a location associated with a vehicle-sharing session request, a vehicle type, or a combination thereof. In one form, the preconditioning parameters may include, but are not limited to: a setpoint temperature of the vehicle, a defrost setting of the vehicle, a seat position of the vehicle, an audio setting of the vehicle, and/or a previously inputted setpoint temperature, defrost setting, seat position, or audio setting.

In one form, the client device 30 may provide the vehicle-sharing request to the fleet management system 20. In response to receiving the vehicle-sharing request, the fleet management system 20 identifies one of the vehicles from the vehicle fleet 40, such as the vehicle 40-1. Furthermore, the fleet management system 20 preconditions the vehicle 40-1 based on the session parameters of the vehicle-sharing request, preconditioning parameters, and/or sensor data associated with the vehicle-sharing session, as described below in further detail.

Figure 2:
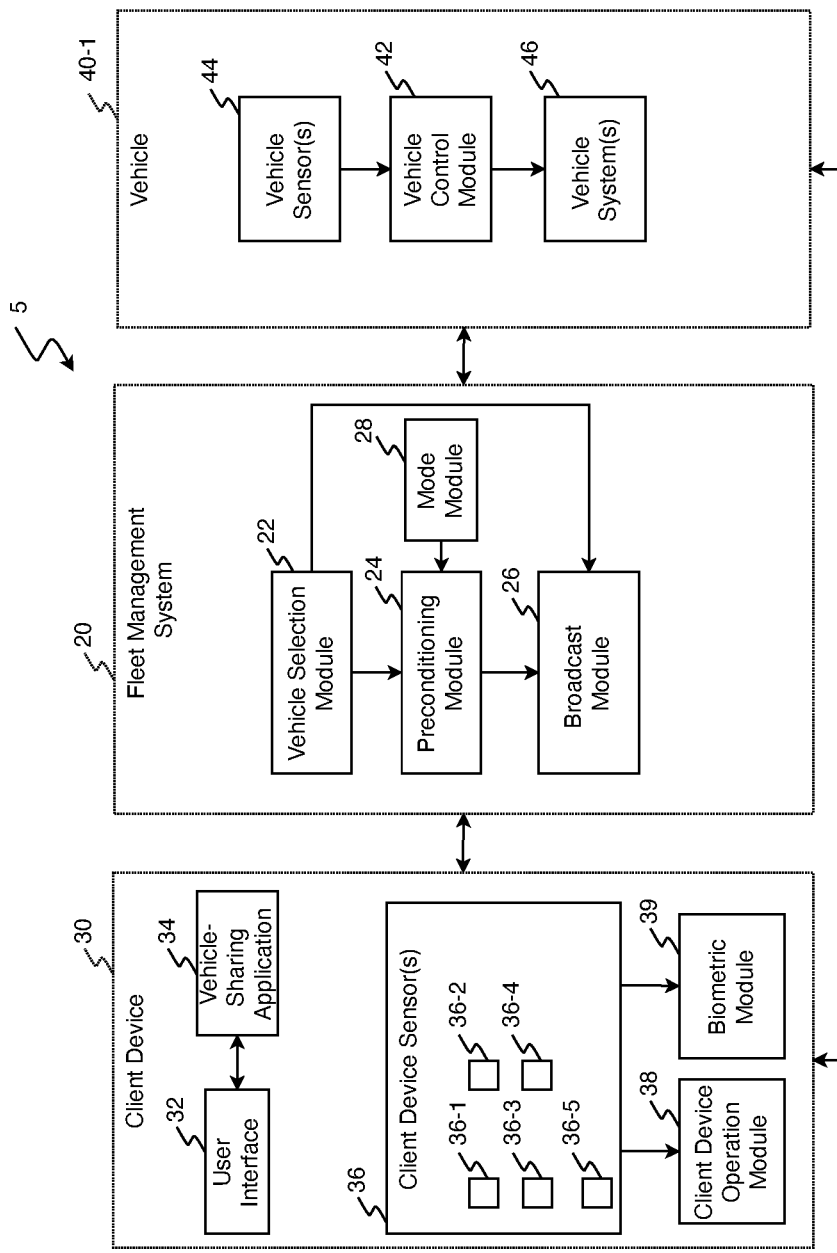
FIG. 2 is a functional block diagram of a vehicle-sharing system in accordance with the teachings of the present disclosure.

Referring to FIG. 2, a functional block diagram of the fleet management system 20, the client device 30, and the vehicle 40-1 is shown. While the fleet management system 20, the client device 30, and the vehicle 40-1 are illustrated as separate systems, it should be understood that any one of the components of the fleet management system 20, the client device 30, the vehicle 40-1 can be provided at other locations and communicably coupled accordingly. In order to execute the functionality described herein, the modules and control systems of the fleet management system 20, the client device 30, and the vehicle 40-1 may include one or more processor circuits that execute machine-readable instructions stored in a nontransitory computer-readable medium, such as a read-only memory (ROM) circuit and/or a random-access memory (RAM) circuit.

In one form, the client device 30 includes a user interface 32, a vehicle-sharing application 34, one or more client device sensors 36, a client device operation module 38, and a biometric module 39. In one form, the user interface 32 includes a graphical user interface display and/or an audio system to provide inputs received from the user 10 to the vehicle-sharing application 34. As an example, the user interface 32 may include a touchscreen device to receive inputs corresponding to the session parameters. As another example, the user interface 32 includes an augmented reality (AR) device configured to receive inputs corresponding to the session parameters using an AR overlay operation. As an additional example, the user interface 32 may include microphones, speakers, and/or natural language user interface systems for receiving voice queries corresponding to the session parameters.

In one form, the vehicle-sharing application 34 is configured to transmit a vehicle-sharing request to the fleet management system 20 for initiating a vehicle-sharing session based on the session parameters defined by the user 10 via the user interface 32. In one form, the vehicle-sharing application 34 receives a digital key from the fleet management system 20 and initiates the vehicle-sharing session in response to the fleet management system 20 preconditioning the vehicle 40-1, as described below in further detail.

In one form, the client device sensors 36 include sensors configured to generate various operational information of the client device 30. As an example, the client device sensors 36 include a location sensor 36-1 configured to generate location data associated with the client device 30, such as a global navigation satellite system (GNSS) sensor. As another example, the client device sensors 36 include an accelerometer 36-2 configured to generate speed and/or directional information associated with the client device 30. It should be understood that the client device sensors 36 may include various sensors for generating various operational information of the client device 30 and are not limited to the examples provided herein. In one form, the client device operation module 38 determines a location, direction, and/or speed of the client device 30 based on the sensor data from the location sensor 36-1 and the accelerometer 36-2 using known location, position, and/or trajectory determination techniques. Furthermore, the client device operation module 38 provides the determined location, direction and/or speed to the fleet management system 20 for remotely activating/controlling various systems of the vehicle 40-1, as described below in further detail.

In one form, the client device sensors 36 include biometric sensors configured to generate various biometrics associated with the user 10 of the client device 30. As an example, the client device sensors 36 include an electrocardiogram (ECG) sensor 36-3 configured to measure cardiac responses to physical exertion by the user 10, a photoplethysmography (PPG) sensor 36-4 to measure the heart rate of the user 10, and/or a temperature sensor 36-5 to measure a body temperature of the user 10. It should be understood that the client device sensors 36 may include various other biometric sensors and are not limited to the examples provided herein. In one form, the biometric module 39 determines one or biometrics of the user 10 based on the sensor data from the ECG sensor 36-3, the PPG sensor 36-4, and/or the temperature sensor 36-5 using known biometric data processing techniques. Furthermore, the biometric module 39 provides the determined biometrics of the user 10 to the fleet management system 20 for remotely activating/controlling various systems of the vehicle 40-1, as described below in further detail.

In one form, the vehicle 40-1 includes a vehicle control module 42, one or more vehicle sensors 44, and one or more vehicle systems 46. The vehicle control module 42, the one or more vehicle sensors 44, and the one or more vehicle systems 46 may be communicably coupled using a vehicle interface, which may be, for example, a controller area network (CAN), a local interconnect network (LIN), a clock extension peripheral interface (CXPI) bus, and/or other suitable vehicle communication networks.

Figure 3:
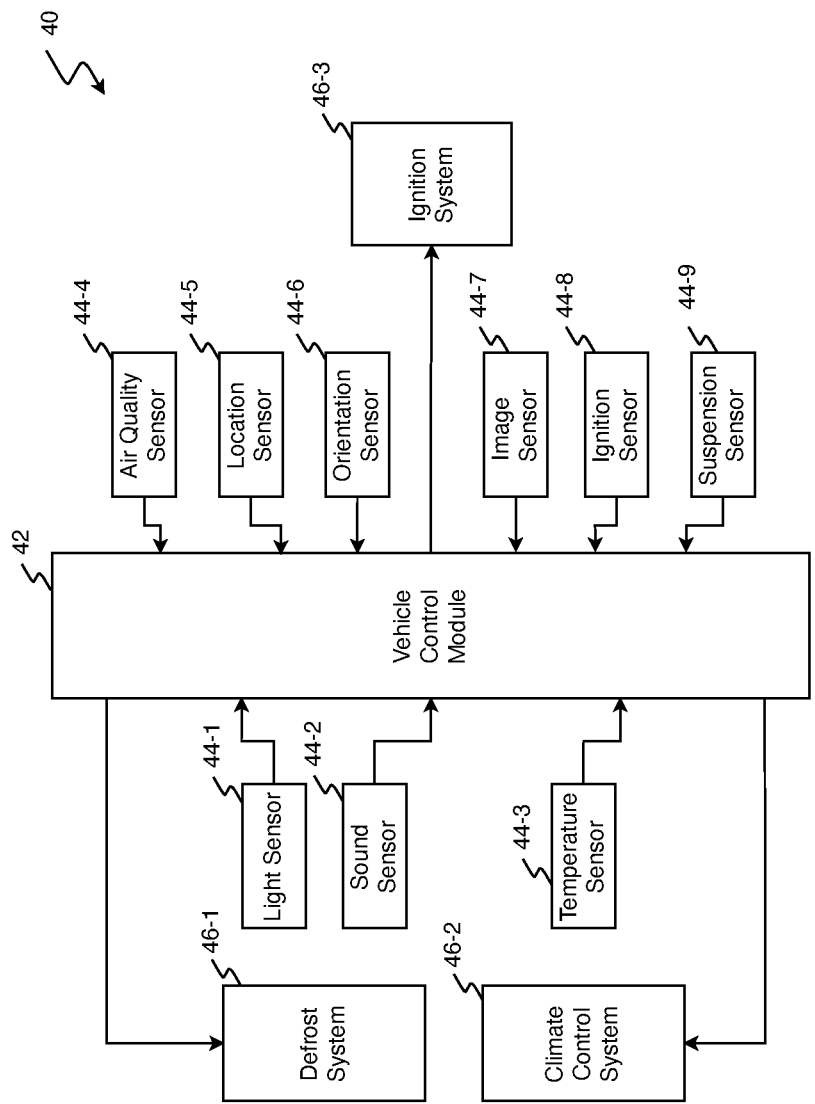
FIG. 3 is a functional block diagram of a vehicle in accordance with the teachings of the present disclosure.

In one form, the vehicle sensors 44 are sensors configured to generate various operational information associated with the vehicle 40-1 and/or an ambient environment of the vehicle 40-1. Referring to FIG. 3, in one form, the one or more vehicle sensors 44 includes a light sensor 44-1, a sound sensor 44-2, a temperature sensor(s) 44-3, and an air quality sensor 44-4. The light sensor 44-1 is mounted on a windshield, rearview mirror, or dashboard of the vehicle 40-1 and is configured to detect ambient light of the vehicle 40-1 (e.g., an infrared sensor). The sound sensor 44-2 is configured to detect ambient sound of the vehicle 40-1 (e.g., a transducer). The temperature sensors 44-3 is configured to detect temperature within the vehicle such as a cabin temperature and/or a steering wheel temperature of the vehicle 40-1. The air quality sensor 44-4 is configured to detect oxygen in an exhaust system of the vehicle and/or an ambient environment surrounding the vehicle 40-1 (e.g., a heated exhaust gas oxygen (HEGO) sensor).

In one form, the one or more vehicle sensors 44 may also include a location sensor 44-5, an orientation sensor 44-6, an image sensor 44-7, an ignition sensor 44-8, and a suspension sensor 44-9. The location sensor 44-5 is configured to generate location data associated with the vehicle 40-1 (e.g., a global navigation satellite system (GNSS) sensor). The orientation sensor 44-6 is configured to generate pose data associated with the vehicle 40-1 (e.g., a magnetometer). The image sensor 44-7 is configured to generate image data of an ambient environment of the vehicle 40-1. The image sensor 44-7 may include, but is not limited to: a two-dimensional (2D) camera, a 3D camera, an infrared sensor, a radar scanner, a laser scanner, a light detection and ranging (LIDAR) sensor, and an ultrasonic sensor. The ignition sensor 44-8 is configured to detect whether the vehicle 40-1 is on or off, and the suspension sensor 44-9 is configured to detect movement of suspension components of the vehicle 40-1.

In one form, the one or more vehicle systems 46 may include a defrost system 46-1, a climate control system 46-2, and an ignition system 46-3. While three vehicle systems 46 are shown in FIG. 3, it should be understood that any number and/or types of vehicle systems 46 may be included and are not limited to the examples described herein.

Referring to FIG. 2 in one form, the fleet management system 20 includes a vehicle selection module 22, a preconditioning module 24, a broadcast module 26, and a mode module 28. In one form, the vehicle selection module 22 receives the vehicle-sharing request from the vehicle-sharing application 34 and selects a vehicle from the vehicle fleet 40 based on the vehicle-sharing request (e.g., vehicle 40-1). Furthermore, the vehicle selection module 22 may reserve a vehicle sharing session based on the vehicle-sharing request.

Prior to initiating the vehicle-sharing session, the preconditioning module 24 is configured to generate a control signal that selectively controls one of the vehicle systems 46 based on one or more parameters. In one form, the parameters include: the session parameters; preconditioning parameters associated with the vehicle-sharing session; operational information associated with the vehicle 40-1 and/or the client device 30; prediction models based on historical operational information associated with the vehicle 40-1 and/or the client device 30; and/or control rules provided by the mode module 28. Furthermore, prior to initiating the vehicle-sharing session, the broadcast module 26 is configured to broadcast the control signal to the vehicle 40-1.

In one form, the control rules of the mode module 28 may include generating a control signal that selectively inhibits the remote activation of the ignition system 46-3 (and thus the control of the defrost system 46-1 and/or the climate control system 46-2) if the vehicle control module 42 determines the vehicle 40-1 is located in an enclosed environment, such as a parking garage. In one form, the control rules may include generating a control signal that does not provide for selectively inhibiting the remote activation of the ignition system 46-3 if the user 10 inputs a preconditioning parameter corresponding to ignoring the location determination of the vehicle 40-1 (e.g., the user 10 generates an input corresponding to paying a monetary fee to precondition the vehicle 40-1 in an enclosed location). It should be understood that the mode module 28 may include various control rules and is not limited to the examples described herein.

Various preconditioning examples are provided below to illustrate the operation of the vehicle-sharing system 5 of the present disclosure. It should be understood that other preconditioning parameters can be used, and the present disclosure is not limited to the examples described herein.

In an example implementation, a vehicle-sharing request from the vehicle sharing application 34 is provided to the preconditioning module 24 and requests, as the preconditioning parameter, activation of the defrost system 46-1 to remove ice and/or snow on the windshield of the vehicle 40-1. The preconditioning module 24 also receives information from the vehicle control module 42 indicating an accumulation of snow and/or ice on the windshield of the vehicle 40-1. As an example, the vehicle control module 42 determines that an accumulation of snow and/or ice on the windshield is present based on infrared reflection data from the light sensor 44-1 and/or sound data obtained from the sound sensor 44-2 indicating that windshield wipers of the vehicle 40-1 are interacting with the snow/ice. As such, the preconditioning module 24 generates and broadcasts a control signal based on the request to activate the defrost system 46-1 and the determined accumulation of snow/ice to control the defrost system 46-1 such that the snow and/or ice is melted prior to the user 10 initiating the vehicle-sharing session.

In another example, a vehicle-sharing request from the vehicle sharing application 34 is provided to the preconditioning module 24 and requests, as the preconditioning parameter, activation of the climate control system 46-2 for setting the cabin temperature of the vehicle 40-1 to a requested cabin temperature. The preconditioning module 24 receives information from the vehicle control module 42 indicating a cabin temperature, steering wheel temperature, and/or seat temperature of the vehicle 40-1. As an example, the vehicle control module 42 determines the cabin temperature, the steering wheel temperature, and/or the seat temperature of the vehicle 40-1 based on the temperature data generated by the one or more temperature sensors 44-3. As such, the preconditioning module 24 generates and broadcasts a control signal based on the requested temperature and the temperature data to control the climate control system 46-2 such that cabin temperature is equal to the requested cabin temperature prior to the user 10 initiating the vehicle-sharing session.

As another example, a vehicle-sharing request provided to the preconditioning module 24 requests, as the preconditioning parameter, activation of the climate control system 46-2 for setting the cabin temperature of the vehicle 40-1 to a requested cabin temperature. The preconditioning module 24 receives the location, direction, and/or speed of the client device 30 as determined by the client device operation module 38. As an example, the location, direction, and/or speed of the client device 30 may indicate an estimated time of arrival of the user 10 at a location proximate the vehicle 40-1. As such, the preconditioning module 24 generates and broadcasts a control signal based on the requested temperature and the location, direction, and/or speed of the client device 30 to control the climate control system 46-2 such that cabin temperature is equal to the requested cabin temperature prior to the user 10 initiating the vehicle-sharing session.

In another example, a vehicle-sharing request provided to the preconditioning module 24 requests, as the preconditioning parameter, activation of the climate control system 46-2 to decrease a cabin temperature of the vehicle 40-1. The preconditioning module 24 receives the biometrics of the user 10 as determined by the biometric module 39. As an example, the biometrics of the user 10 indicate that a body temperature of the user 10 is high based on the heart activity of the user 10 (as indicated by the ECG sensor 36-3 and/or the PPG sensor 36-4) and the measured temperature of the user 10 (as indicated by the temperature sensor 36-5). As such, the preconditioning module 24 generates and broadcasts a control signal based on the preconditioning parameter and the biometrics of the user 10 to control the climate control system 46-2 such that cabin temperature decreases to a sufficient temperature prior to the user 10 initiating the vehicle-sharing session.

In one form, the vehicle control module 42 may determine that the vehicle 40-1 is in an enclosed environment and thus, based on the control rules of the mode module 28, the preconditioning module 24 inhibits activation of the vehicle 40-1. For instance, in one example, the vehicle control module 42 determines that the vehicle 40-1 is in an enclosed environment in response to the air quality sensor 44-4 indicating a concentration of contaminants in the ambient air surrounding the vehicle 40-1 is greater than a threshold concentration value. As such, the preconditioning module 24 may generate and broadcast a control signal that, in accordance with the control rules of the mode module 28, inhibits (or periodically inhibits) the remote activation of the ignition system 46-3.

In one variation, the vehicle control module 42 may determine the vehicle 40-1 is in an enclosed environment in response to the GNSS data generated by the location sensor 44-5 indicating that the vehicle 40-1 is in a parking garage or other type of enclosed environment. In addition to the location data, the vehicle control module 42 may validate that the vehicle 40-1 is in the enclosed environment in response to the orientation data generated by the orientation sensor 44-6 indicating that the vehicle 40-1 is not oriented near and/or adjacent to an opening of a structure (e.g., a window of a parking garage). As such, the preconditioning module 24 may generate and broadcast a control signal that, in accordance with the control rules of the mode module 28, inhibits (or periodically inhibits) the remote activation of the ignition system 46-3.

In yet another variation, the vehicle control module 42 may determine the vehicle 40-1 is in an enclosed environment in response to a series of light data generated by the light sensors 44-1 indicating a transition from a bright, uncovered environment to a dark, enclosed environment. Additionally or alternatively, the vehicle control module 42 may determine the vehicle 40-1 is in an enclosed environment if the light data corresponds to a dark, enclosed environment during daylight hours. As such, the preconditioning module 24 may generate and broadcast a control signal that, in accordance with the control rules of the mode module 28, inhibits (or periodically inhibits) the remote activation of the ignition system 46-3.

In another variation, the vehicle control module 42 may determine the vehicle 40-1 is in an enclosed environment in response to image data generated by the image sensor 44-7 indicating that the vehicle 40-1 is in an enclosed environment. As an example, the vehicle control module 42 may perform known image processing routines (e.g., a difference-based image processing routine, a semantic-based image processing routine, among others) on the image data to determine whether the vehicle 40-1 is in the enclosed environment. As such, the preconditioning module 24 may generate and broadcast a control signal that, in accordance with the control rules of the mode module 28, inhibits (or periodically inhibits) the remote activation of the ignition system 46-3.

In yet another variation, the vehicle control module 42 may determine the vehicle 40-1 is in an enclosed environment in response to sound data generated by the sound sensor 44-2 indicates the vehicle 40-1 is in an enclosed environment. As an example, the vehicle control module 42 may activate a horn of the vehicle 40-1 and perform known sound processing techniques on the resulting sound data to determine whether the vehicle 40-1 is in an enclosed environment. As such, the preconditioning module 24 may generate and broadcast a control signal that, in accordance with the control rules of the mode module 28, inhibits (or periodically inhibits) the remote activation of the ignition system 46-3.

As another variation, the vehicle control module 42 may determine the vehicle 40-1 is in an enclosed environment in response to recently obtained suspension data generated by the suspension sensor 44-9 indicating the vehicle 40-1 has traveled along a road having a grade corresponding to transitions between levels of a parking garage. Furthermore, the vehicle control module 42 may determine the vehicle 40-1 is in an enclosed environment in response to recently obtained suspension data indicating force events corresponding to rumble strips in a parking garage. As such, the preconditioning module 24 may generate and broadcast a control signal that, in accordance with the control rules of the mode module 28, inhibits (or periodically inhibits) the remote activation of the ignition system 46-3.

While each of the examples of processing the sensor data to determine whether the vehicle 40-1 is in the enclosed environment are described individually, it should be understood that any of the above examples may be selectively combined to determine whether the vehicle 40-1 is in the enclosed environment.

Figure 4:
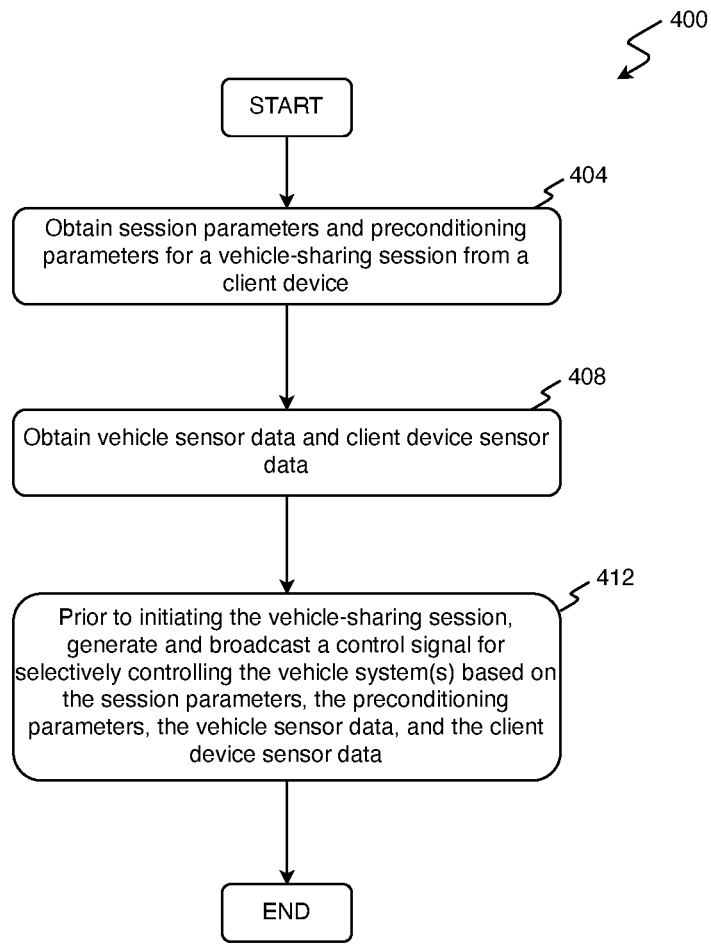
FIG. 4 illustrates an example control routine performed by a vehicle-sharing system in accordance with the teachings of the present disclosure.

With reference to FIG. 4, an example routine 400 performed by the fleet management system 20 is shown. At 404, the fleet management system 20 obtains the session parameters and the preconditioning parameters from the client device 30 and more particularly, the vehicle-sharing application 34. At 408, the fleet management system 20 obtains vehicle sensor data from the vehicle 40-1 and the client device sensor data from the client device 30. At 412, the fleet management system 20, prior to initiating the vehicle-sharing session, generates and broadcasts a control signal for selectively controlling the one or more vehicle systems 46 of the vehicle 40-1 based on the session parameters, the preconditioning parameters, the vehicle sensor data, and the client device sensor data.

Figure 5:
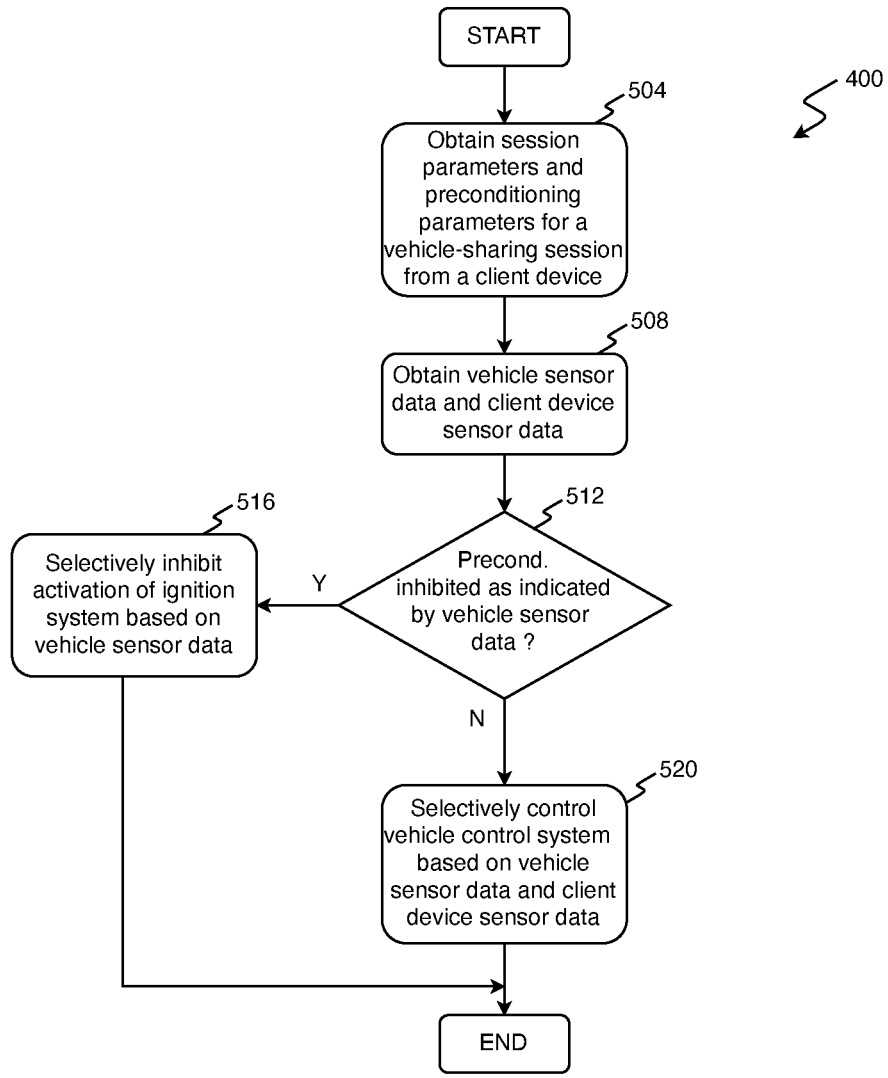
FIG. 5 illustrates another example control routine performed by a vehicle-sharing system in accordance with the teachings of the present disclosure.

With reference to FIG. 5, an example routine 500 performed by the vehicle-sharing system 5 is shown. At 504, the fleet management system 20 obtains the session parameters and the preconditioning parameters for a vehicle-sharing session from the client device 30. At 508, the fleet management system 20 obtains vehicle sensor data from the vehicle 40-1 and the client device sensor data from the client device 30. At 512, the fleet management system 20 determines whether the vehicle sensor data corresponds to selectively inhibiting the remote activation of the ignition system 46-3. If the vehicle sensor data corresponds to selectively inhibiting the remote activation of the ignition system 46-3, the routine 500 proceeds to 516, where the vehicle 40-1 selectively inhibits the activation of the ignition system 46-3 based on the vehicle sensor data. If the preconditioning parameters do not require activation of the ignition system 46-3, the routine 500 proceeds to 520, where the vehicle 40-1 selectively controls the one or more vehicle systems 46 based on the vehicle sensor data and the client device sensor data.

It should be readily understood that routines 400, 500 are example control routines and other control routines may be implemented.

The fleet management system 20 described herein is configured to generate and transmit a control signal based on session parameters associated with a vehicle-sharing session, preconditioning parameters associated with the vehicle-sharing session, and sensor data associated with the vehicle-sharing session. The sensor data includes sensor data from a vehicle and/or a client device associated with the vehicle-sharing session. As such, the fleet management system 20 is configured to remotely precondition the vehicle 40-1 while accommodating for the location and the environment surrounding the vehicle 40-1.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice, manufacturing technology, and testing capability.

As used herein, the phrase at least one of A, B, and C should be construed to mean a logical (A OR B OR C), using a non-exclusive logical OR, and should not be construed to mean "at least one of A, at least one of B, and at least one of C."

The description of the disclosure is merely exemplary in nature and, thus, variations that do not depart from the substance of the disclosure are intended to be within the scope of the disclosure. Such variations are not to be regarded as a departure from the spirit and scope of the disclosure.

In the figures, the direction of an arrow, as indicated by the arrowhead, generally demonstrates the flow of information (such as data or instructions) that is of interest to the illustration. For example, when element A and element B exchange a variety of information, but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, the term "module" and/or "controller" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The term memory is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks, flowchart components, and other elements described above serve as software specifications, which can be translated into the computer programs by the routine work of a skilled technician or programmer.

What is claimed is:

1. A method of remotely activating a vehicle system of a vehicle, the vehicle being part of a vehicle-share enterprise, the method comprising:

generating a control signal based on session parameters associated with a vehicle-sharing session, preconditioning parameters associated with the vehicle-sharing session, and sensor data associated with the vehicle-sharing session, wherein the sensor data includes vehicle sensor data from one or more sensors of the vehicle associated with the vehicle-sharing session and client device sensor data from one or more sensors of a client device, said client device sensor data comprises client device location data, client device movement data and biometric data associated with a user of the client device; and prior to initiating the vehicle-sharing session, broadcasting the control signal to the vehicle, wherein the control signal is configured to selectively control the vehicle system. the vehicle sensor data is indicative of a location of the vehicle, an orientation of the vehicle, or a combination thereof;

determining the vehicle is in an enclosed location based on a location sensor, a light sensor, an orientation sensor, an image sensor, a sound sensor, and a suspension sensor; and the control signal includes instructions for inhibiting activating the vehicle based on determining the vehicle is in the enclosed location.

2. The method of claim 1, wherein the session parameters include a start time of the vehicle-sharing session, an end time of the vehicle-sharing session, a monetary cost of the vehicle-sharing session, a location associated with a vehicle-sharing session request, or a combination thereof.

3. The method of claim 1, wherein the preconditioning parameters include a setpoint temperature of the vehicle, a defrost setting of the vehicle, a seat position of the vehicle, an audio setting of the vehicle, or a combination thereof.

4. The method of claim 1, wherein:

the vehicle sensor data is indicative of an accumulation of snow, an accumulation of ice, or a combination thereof;

the one or more sensors of the vehicle include at least one of a light sensor, a sound sensor, or a combination thereof; and the control signal includes instructions for selectively controlling a defrost system, as the vehicle system, based on the vehicle sensor data.

5. The method of claim 1, wherein:

the vehicle sensor data is indicative of a cabin temperature of the vehicle;

the one or more sensors of the vehicle include one or more temperature sensors; and the control signal includes instructions for selectively controlling a climate control system, as the vehicle system, based on the vehicle sensor data.

6. The method of claim 1, wherein:
the vehicle sensor data is indicative of a steering wheel temperature of the vehicle, a seat temperature of the vehicle, or a combination thereof;
the one or more sensors of the vehicle include one or more temperature sensors; and
the control signal includes instructions for selectively controlling a climate control system, as the vehicle system, based on the vehicle sensor data.

7. The method of claim 1, wherein:
the vehicle sensor data is indicative of ambient air characteristics of the vehicle;
the one or more sensors of the vehicle include an air quality sensor; and
the control signal includes instructions for selectively controlling an ignition system, as the vehicle system, based on the vehicle sensor data.

8. The method of claim 1, wherein:
the client device sensor data is indicative of a location of the client device, a speed of the client device, a direction of the client device, or a combination thereof; and
the one or more sensors of the client device include a location sensor, an accelerometer, or a combination thereof.

9. The method of claim 1, wherein:
the client device sensor data is indicative of one or more biometrics associated with a user of the client device; and
the one or more sensors of the client device include a biometric sensor.

10. The method of claim 1, wherein the control signal is further based on a prediction model associated with the vehicle, the client device, or a combination thereof.

11. A method of remotely activating a vehicle system of a vehicle, the vehicle being part of a vehicle-share enterprise, the method comprising:
generating a control signal based on session parameters associated with a vehicle-sharing session, preconditioning parameters associated with the vehicle-sharing session, and sensor data associated with the vehicle-sharing session, wherein the sensor data includes vehicle sensor data from one or more sensors of the vehicle associated with the vehicle-sharing session and client device sensor data from one or more sensors of a client device, said client device sensor data comprises client device location data, client device movement data and biometric data associated with a user of the client device; and
prior to initiating the vehicle-sharing session:
determining the vehicle is in an enclosed location based on a location sensor, a light sensor, an orientation sensor, an image sensor, a sound sensor, and a suspension sensor; and
broadcasting the control signal to the vehicle; and
inhibiting activating the vehicle based on determining the vehicle is in the enclosed location based on the control signal.

12. The method of claim 11, wherein:
the session parameters include a start time of the vehicle-sharing session, an end time of the vehicle-sharing session, a monetary cost of the vehicle-sharing session, a location associated with a vehicle-sharing session request, or a combination thereof; and
the preconditioning parameters include a setpoint temperature of the vehicle, a defrost setting of the vehicle, a seat position of the vehicle, an audio setting of the vehicle, or a combination thereof.

13. The method of claim 11, wherein:
the vehicle sensor data is indicative of an accumulation of snow, an accumulation of ice, or a combination thereof;
the one or more sensors of the vehicle include at least one of a light sensor, a sound sensor, or a combination thereof; and
the control signal includes instructions for selectively controlling a defrost system, as the vehicle system, based on the vehicle sensor data.

14. The method of claim 11, wherein:
the vehicle sensor data is indicative of a cabin temperature of the vehicle, a steering wheel temperature of the vehicle, a seat temperature of the vehicle, or a combination thereof;
the one or more sensors of the vehicle include one or more temperature sensors; and
the control signal includes instructions for selectively controlling a climate control system, as the vehicle system, based on the vehicle sensor data.

15. The method of claim 11, wherein:
the vehicle sensor data is indicative of ambient air characteristics of the vehicle;
the one or more sensors of the vehicle include an air quality sensor; and
the control signal includes instructions for selectively controlling an ignition system, as the vehicle system, based on the vehicle sensor data.

16. The method of claim 11, wherein:
the client device sensor data is indicative of a location of the client device, a speed of the client device, a direction of the client device, or a combination thereof; and
the one or more sensors of the client device include a location sensor, an accelerometer, or a combination thereof.

17. A system of remotely activating a vehicle system of a vehicle, the vehicle being part of a vehicle-share enterprise, the system comprising:
a processor; and
a non-transitory computer-readable medium including machine-readable instructions that are executable by the processor, wherein the machine-readable instructions include:
generating a control signal based on session parameters associated with a vehicle-sharing session, preconditioning parameters associated with the vehicle-sharing session, and sensor data associated with the vehicle-sharing session, wherein the sensor data includes vehicle sensor data from one or more sensors of the vehicle associated with the vehicle-sharing session and, client device sensor data from one or more sensors of a client device, said client device sensor data comprises client device location data, client device movement data and biometric data associated with a user of the client device; and
prior to initiating the vehicle-sharing session:
determining the vehicle is in an enclosed location based on a location sensor, a light sensor, an orientation sensor, an image sensor, a sound sensor, and a suspension sensor; and
broadcasting the control signal to the vehicle; and
inhibiting activating the vehicle based on determining the vehicle is in the enclosed location based on the control signal.

18. The method of claim 1 where generating the control signal comprises generating the control signal from the client device movement data from an accelerometer to generate speed or directional information.

19. The method of claim 1 where generating the control signal comprises generating the control signal from the biometric data of the client comprising an electrocardiogram sensor, a photoplethysmography sensor, a body temperature sensor and combinations thereof.

20. The method of claim 11 where generating the control signal comprises generating the control signal from the location data from a location sensor.

21. The method of claim 11 where generating the control signal comprises generating the control signal from the client device movement data from an accelerometer to generate speed or directional information.

22. The method of claim 11 where generating the control signal comprises generating the control signal from the biometric data of the client comprising an electrocardiogram sensor, a photoplethysmography sensor, a body temperature sensor and combinations thereof.

23. The system of claim 17 wherein the client device sensor data comprises the location data from a location sensor.

24. The system of claim 17 wherein the client device sensor data comprises the client device movement data from an accelerometer to generate speed or directional information.

25. The system of claim 17 wherein the client device sensor data comprises the biometric data of the client from an electrocardiogram sensor, a photoplethysmography sensor, a body temperature sensor and combinations thereof.

* * * * *